(12) United States Patent
Vent (10) Patent No.: US 7,351,574 B2
(45) Date of Patent: Apr. 1, 2008

(54) LOADING AND EJECTION SYSTEMS FOR BIOLOGICAL GROWTH PLATE SCANNER

(75) Inventor: Albert Vent, Eschweiler (DE)

(73) Assignee: 3M Innovative Properties Company, Saint Paul, MN (US)

( * ) Notice: Subject to any disclaimer, the term of this patent is extended or adjusted under 35 U.S.C. 154(b) by 474 days.

(21) Appl. No.: 10/306,665

(22) Filed: Nov. 27, 2002

(65) Prior Publication Data

US 2004/0101952 A1    May 27, 2004

(51) Int. Cl.
*C12M 1/36* (2006.01)

(52) U.S. Cl. .............................. 435/286.2; 435/288.7; 435/303.1; 422/65; 422/82.05

(58) Field of Classification Search ..................... None
See application file for complete search history.

(56) References Cited

U.S. PATENT DOCUMENTS

| | | |
|---|---|---|
| 3,493,772 A | 2/1970 | Daughters et al. |
| 3,811,036 A | 5/1974 | Perry |
| 3,962,040 A | 6/1976 | Campbell et al. |
| 4,118,280 A | 10/1978 | Charles et al. |
| 4,160,601 A | 7/1979 | Jacobs |
| 4,353,988 A | 10/1982 | Couse et al. |
| 4,591,567 A | 5/1986 | Britten et al. |
| 4,637,053 A | 1/1987 | Schalkowsky |
| 4,720,463 A | 1/1988 | Farber et al. |
| 4,724,215 A | 2/1988 | Farber et al. |
| 4,817,785 A | 4/1989 | Farber et al. |
| 4,856,073 A | 8/1989 | Farber et al. |
| 5,117,467 A | 5/1992 | Misaki et al. |
| 5,290,701 A | 3/1994 | Wilkins |
| 5,329,686 A | 7/1994 | Kildal et al. |
| 5,364,766 A | 11/1994 | Mach et al. |
| 5,366,873 A | 11/1994 | Eden et al. |
| 5,372,485 A | 12/1994 | Sumser et al. |
| 5,372,936 A | 12/1994 | Fraatz et al. |
| 5,375,043 A | 12/1994 | Tokunaga |
| 5,403,722 A | 4/1995 | Floeder et al. |

(Continued)

FOREIGN PATENT DOCUMENTS

DE         19819144         4/1998

(Continued)

OTHER PUBLICATIONS

Product brochure entitled "Powerful data handling for GLP conformance" by ProtoCOL, Synbiosis, a division of Synoptic Ltd., Cambridge, UK (4 pgs.).

(Continued)

*Primary Examiner*—David Redding (57) ABSTRACT

The invention is directed to a biological scanner for scanning biological growth plates. A biological growth plate can be loaded into the biological scanner. Upon loading of a biological growth plate, the biological scanner generates an image of the plate and may perform an analysis of the image. Various embodiments are directed to loading features that facilitate automated loading and proper positioning of a plate within the biological scanner, and ejection features that facilitate the automated ejection of the plate from the scanner. Additional embodiments are directed to features that allow a scanner unit of the biological scanner to be attached to a mounting platform of the scanner in different possible configurations.

11 Claims, 11 Drawing Sheets

U.S. PATENT DOCUMENTS

| | | | |
|---|---|---|---|
| 5,428,690 | A | 6/1995 | Bacus et al. |
| 5,448,652 | A | 9/1995 | Vaidyanathan et al. |
| 5,510,246 | A | 4/1996 | Morgan |
| 5,539,517 | A | 7/1996 | Cabib et al. |
| 5,573,950 | A | 11/1996 | Graessle et al. |
| 5,671,290 | A | 9/1997 | Vaidyanathan |
| 5,694,478 | A | 12/1997 | Braier et al. |
| 5,721,435 | A | 2/1998 | Troll |
| 5,723,308 | A | 3/1998 | Mach et al. |
| 5,744,322 | A | 4/1998 | Krejcarek et al. |
| 5,747,333 | A | 5/1998 | Jungmann-Campello et al. |
| 5,781,311 | A | 7/1998 | Inoue et al. |
| 5,787,189 | A | 7/1998 | Lee et al. |
| 5,817,475 | A | 10/1998 | Gibbs et al. |
| 5,995,645 | A | 11/1999 | Soenksen et al. |
| 6,002,789 | A | 12/1999 | Olsztyn et al. |
| 6,096,272 | A | 8/2000 | Clark et al. |
| 6,107,054 | A | 8/2000 | Gibbs |
| 6,238,879 | B1 | 5/2001 | Gibbs |
| 6,243,486 | B1 | 6/2001 | Weiss .................. 382/133 |
| 6,271,022 | B1 | 8/2001 | Bochner |
| 6,372,485 | B1 | 4/2002 | Clark et al. |
| 6,381,353 | B1 | 4/2002 | Weiss .................. 382/133 |
| 6,418,180 | B1 | 7/2002 | Weiss .................... 377/6 |
| 6,485,979 | B1 | 11/2002 | Kippenhan et al. |
| 6,488,890 | B1 | 12/2002 | Kirckof |
| 6,642,953 | B1 | 11/2003 | Nieto Velasco et al. |
| 6,673,315 | B2 | 1/2004 | Sheridan et al. |
| 6,690,470 | B1 | 2/2004 | Baer et al. |
| 6,711,283 | B1 | 3/2004 | Soenksen |
| 6,716,588 | B2 | 4/2004 | Sammak et al. |
| 2001/0031502 | A1 | 10/2001 | Watson, Jr. et al. |
| 2001/0041347 | A1 | 11/2001 | Sammak et al. |
| 2002/0064867 | A1 | 5/2002 | Clark et al. |
| 2002/0137091 | A1 | 9/2002 | Luttermann et al. ......... 435/7.1 |
| 2004/0101189 | A1 | 5/2004 | Green et al. |
| 2004/0101951 | A1 | 5/2004 | Vent el al. |
| 2004/0101952 | A1 | 5/2004 | Vent |
| 2004/0101954 | A1 | 5/2004 | Graessie et al. |
| 2004/0102903 | A1 | 5/2004 | Graessle et al. |

FOREIGN PATENT DOCUMENTS

| | | |
|---|---|---|
| EP | 0 008 826 A2 | 3/1980 |
| EP | 0 088 601 A1 | 9/1983 |
| EP | 0 397 256 A2 | 11/1990 |
| EP | 0 397 256 A3 | 11/1990 |
| EP | 0 429 030 A2 | 5/1991 |
| EP | 0 429 030 A3 | 5/1991 |
| EP | 0 193 385 B1 | 7/1992 |
| EP | 0 547 709 A2 | 6/1993 |
| EP | 0 547 709 A3 | 6/1993 |
| EP | 0 819 930 A2 | 1/1998 |
| EP | 1 074 610 B1 | 3/2006 |
| GB | 2 249 829 A | 5/1992 |
| JP | 60-83597 | 5/1985 |
| JP | 5-249105 | 9/1993 |
| JP | 2001-242082 | 7/2001 |
| WO | WO 92/12233 | 7/1992 |
| WO | WO 94/01528 | 1/1994 |
| WO | WO 94/26926 | 11/1994 |
| WO | WO 95/16768 | 6/1995 |
| WO | WO 98/53301 | 11/1998 |
| WO | WO 98/59314 | 12/1998 |
| WO | WO 99/28436 | 6/1999 |
| WO | WO 00/32807 | 6/2000 |
| WO | WO 00/49129 | 8/2000 |
| WO | WO 00/49130 | 8/2000 |
| WO | WO 00/65094 | 11/2000 |
| WO | WO 01/83673 A2 | 11/2001 |
| WO | WO 02/090966 | 1/2002 |
| WO | WO 03/014400 | 2/2003 |
| WO | WO 03/038413 | 5/2003 |

OTHER PUBLICATIONS

Product brochure entitled "Efficient Batch Handling" by ProtoZONE, Synbiosis, a division of Synoptic Ltd., Cambridge, UK (4 pgs).

Product brochure entitled "Petrifilm™ Information Management System—Reduce Operational Costs and Increase Productivity"; 3M Microbiology Products; 1999; 70-2009-1996-0; (3 pgs.).

Prosecution history of U.S. Appl. No. 10/306,416 including: Restriction Requirement dated Sep. 1, 2005 Response to Restriction Requirement dated Sep. 26, 2005 Non-Final Rejection dated Dec. 30, 2005 Amendment dated Mar. 10, 2006 Examiner Interview dated Aug. 7, 2006 Notice of Allowance dated Aug. 7, 2006 Request for Continued Examination dated Sep. 6, 2006 Non-Final Rejection dated Nov. 13, 2006 Amendment dated Feb. 13, 2007.

Gilchrist et al., "Spiral Plate Method for Bacterial Determination", Applied Microbiology, Feb. 1973, vol. 25, No. 2, pp. 244-252.

Corkidi et al.; "*Covasiam: an Image Analysis Method That Allows Detection of Confluent Micobial Colonies and Colonies of Various Sizes for Automated Counting*", Applied and enviromental Microbiology, vol. 64, No.4, Apr. 1998, pp. 1400-1404.

Ilya et al.; "Streamlines Yeast Colorimetric Reporter Activity Assaya Using Scanners and Plate Readers", BioTechniques, vol. 29, No. 2, Aug. 2000.

K.M. Wright et al., "Determination of Mean Growth Parameters of Bacterial Colonies Immobilized in Gelatin Gel Using a Laser Gel-Casset Scanner", International Journal of Food Microbiology, 2000, pp. 75-89.

LOADING AND EJECTION SYSTEMS FOR BIOLOGICAL GROWTH PLATE SCANNER

FIELD

The invention relates to techniques for analysis of biological growth plates to detect and enumerate bacteria or other biological agents in food samples, laboratory samples, and the like.

BACKGROUND

Biological safety is a paramount concern in modern society. Testing for biological contamination in foods or other materials has become an important, and sometimes mandatory requirement for developers and distributors of food products. Biological testing is also used to identify bacteria or other agents in laboratory samples such as blood samples taken from medical patients, laboratory samples developed for experimental purposes, and other types of biological samples. Various techniques and devices can be utilized to improve biological testing and to streamline and standardize the biological testing process.

In particular, a wide variety of biological growth plates have been developed. As one example, biological growth plates have been developed by 3M Company (hereafter "3M") of St. Paul, Minn. Biological growth plates are sold by 3M under the trade name PETRIFILM plates. Biological growth plates can be utilized to facilitate the rapid growth and detection of bacteria or other biological agents commonly associated with food contamination, including, for example, aerobic bacteria, *E. coli*, coliform, enterobacteriaceae, yeast, mold, *Staphylococcus aureus, Listeria, Campylobacter,.* The use of PETRIFILM plates, or other growth media, can simplify bacterial testing of food samples.

Biological growth plates can be used to enumerate or identify the presence of bacteria so that corrective measures can be performed (in the case of food testing) or proper diagnosis can be made (in the case of medical use). In other applications, biological growth plates may be used to rapidly grow bacteria or other biological agents in laboratory samples, e.g., for experimental purposes.

Biological scanners refer to devices used to scan or count bacterial colonies, or the amount of a particular biological agent on a biological growth plate. For example, a food sample or laboratory sample can be placed on a biological growth plate, and then the plate can be inserted into an incubation chamber. After incubation, the biological growth plate can be placed into the biological scanner for automated detection and enumeration of bacterial growth. In other words, biological scanners automate the detection and enumeration of bacteria or other biological agents on a biological growth plate, and thereby improve the biological testing process by reducing human error.

SUMMARY

In general, the invention is directed to a biological scanner for biological growth plates. A biological growth plate is inserted into the biological scanner. Upon insertion of the biological growth plate, the biological scanner generates an image of the plate and performs an analysis of the image. For example, the amount of biological agents that appear in the image, such as a number of bacteria colonies, can be counted or otherwise determined using image processing and analysis routines performed by the biological scanner. In this manner, the biological scanner automates the analysis of biological growth plates.

The biological scanner may incorporate an automated loading mechanism and an automated ejection mechanism to facilitate handling and analysis of biological growth plates by the scanner. The automated loading mechanism may be configured to draw the growth plate into the scanner and place the growth plate in a scanning position. In addition, the biological scanner may include a multiple orientation mounting platform that permits the scanner to be selectively placed in different positions for convenience and space requirements. The mounting platform may cooperate with the ejection mechanism to permit selection of the position of an ejection port for exit of the biological growth plate following analysis.

In one embodiment, the invention provides a biological scanner for biological growth plates comprising a drawer that opens to receive a biological growth plate and closes to move the plate into the scanner. The biological scanner may also include an apparatus, such as a clamp, pincer, securing lever, or the like, to temporarily hold the plate at a location inside the scanner when the drawer is subsequently closed following the movement of the plate into the scanner. The biological scanner may also include a conveyor to remove the plate from the scanner following release of the plate by the apparatus when the drawer is subsequently opened. For example, the drawer may form part of a scanner unit of the biological scanner, and the conveyor may be housed in a mounting platform of the scanner.

In another embodiment, the invention provides a biological scanner for biological growth plates comprising a scanner unit and a mounting platform. The scanner unit receives a biological growth plate to be scan, and the mounting platform ejects the biological growth plate after the plate has been scanned. The scanner unit and the mounting platform can be configured to allow the scanner unit and the mounting platform to be coupled to one another in a plurality of different possible positions relative to one another. By way of example, the scanner unit may house an imaging device and a processor. In addition, the scanner unit may include a drawer that opens to receive the plate and closes to move the plate into the scanner unit. The mounting platform may include a conveyor to eject the plate from a slot in the mounting platform after the plate has been scanned.

In an additional embodiment, the invention provides a biological scanner for biological growth plates comprising a drawer that opens to receive a biological growth plate and closes to move the plate into the scanner. The drawer may include a platform on which the plate rests, and one or more levers to elevate and lower the platform. In addition the biological scanner may include a platen inside the scanner, wherein upon closing the drawer, the lever(s) elevate the platform so that the plate is positioned adjacent the platen.

In an added embodiment, the invention provides a biological scanner for scanning biological growth plates, the scanner comprising a scanner unit that receives a biological growth plate to be scanned, and a mounting platform that ejects the biological growth plate after the plate has been scanned, wherein the scanner unit is positionable on the mounting platform in a plurality of different possible positions.

The invention may provide a number of advantages. For example, the invention may ensure that a biological growth plate can be inserted into a biological scanner, properly positioned within the scanner, imaged or otherwise scanned to identify or enumerate amounts of biological agents, and then ejected from the biological scanner in an automated fashion. In particular, the configurations described herein can automate the insertion and positioning of biological growth plates in a manner that ensures that reliable imaging can occur, thereby improving the integrity of automated scanning of such biological growth plates. Automation of the ejection of the plate from the biological scanner can also simplify the process for a user. Furthermore, the ability to select the position of the scanner unit relative to a mounting platform can allow the biological scanner to be conveniently placed in different laboratory environments that have different layouts or space limitations, e.g., while consistently providing operating power from the mounting platform to the biological scanner unit or from the biological scanner unit to the mounting platform in each position.

Additional details of these and other embodiments are set forth in the accompanying drawings and the description below. Other features, objects and advantages will become apparent from the description and drawings, and from the claims.

DETAILED DESCRIPTION

The invention is directed to a biological scanner for biological growth plates. A biological growth plate can be presented to the biological scanner, which generates an image of the plate and may perform an analysis of the image to detect biological growth.

In particular, the scanner may enumerate or otherwise quantify an amount of biological agents that appear in the image, such as a number of bacteria colonies. In this manner, the biological scanner automates the analysis of biological growth plates, thereby improving such analysis and reducing the possibility of human error.

In addition, the biological scanner may incorporate an automated loading and ejection system that facilitates handling of biological growth plates, as well as a multiple-position mounting platform that enables the biological scanner to occupy different orientations for ease of placement and use in a variety of laboratory environments presenting different space limitations and layout characteristics.

The invention may be useful with a variety of biological growth plates. For example, the invention may be useful with different plate-like devices for growing biological agents to enable detection and/or enumeration of the agents, such as thin-film culture plate devices, Petri dish culture plate devices, and the like. Therefore, the term "biological growth plate" will be used broadly herein to refer to a medium suitable for growth of biological agents to permit detection and enumeration of the agents by a scanner. In some embodiments, the biological growth plate can be housed in a cassette that supports multiple plates, e.g., as described in U.S. Pat. No. 5,573,950 to Graessle et al.

Figure 1:
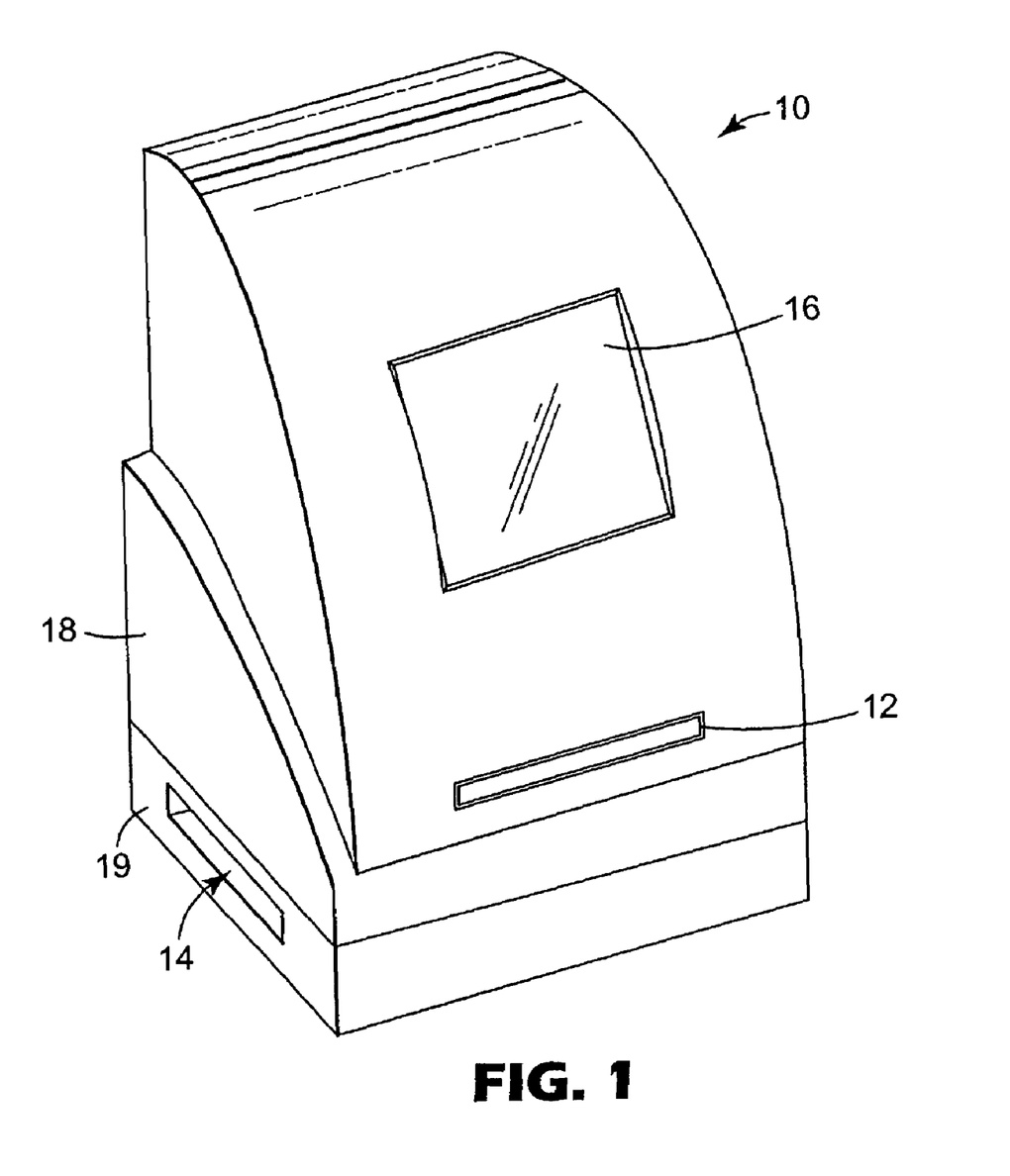
FIG. 1 is a perspective view of a biological scanner in accordance with one embodiment of the invention.

FIG. 1 is a perspective view of a biological scanner 10 in accordance with one embodiment of the invention. As illustrated, biological scanner 10 includes a drawer 12 that receives a biological growth plate, and moves the growth plate into biological scanner 10 for scanning and analysis. Biological scanner 10 also includes an ejection slot 14 through which the growth plate can be ejected following analysis of the biological growth plate. Biological scanner 10 may also include other features, such as a display screen 16 to display the progress or results of analysis of the biological growth plate to a user. Alternatively or additionally, display screen 16 may present to a user an image of the plate inserted into biological scanner 10 via drawer 12. In some embodiments, the displayed image may be optically magnified or digitally scaled upward.

As further shown in FIG. 1, biological scanner 10 may have a two-part design. In particular, biological scanner 10 may have a scanner unit 18 and a mounting platform 19. Scanner unit 18 is mounted on mounting platform 19 and, as will be explained, may occupy multiple orientations relative to the mounting platform. In the example of FIG. 1, scanner unit 18 includes a drawer 12, which extends outward from the scanner unit 18 to receive a biological growth plate and retracts into the scanner unit 18 to place the biological growth plate into scanner 10 for analysis.

Scanner unit 18 also houses an imaging device for scanning the biological growth plate and generating an image of an inserted plate. In addition, scanner unit 18 may house a processor that performs analysis of the scanned image, e.g., in order to determine the level of biological agents in the plate. For example, upon insertion of the biological growth plate via drawer 12, the plate may be positioned adjacent to a platen which is also housed within scanner unit 18. An image of the growth plate can be captured when the plate is positioned within scanner unit 18, e.g., adjacent to platen. Then, when the drawer 12 is subsequently opened, the plate drops downward into the mounting platform 19 for ejection via ejection slot 14.

Mounting platform 19 houses a conveyor that ejects a plate from biological scanner 10 via ejection slot 14. After a biological growth plate is inserted into drawer 12, moved into scanner unit 18, and scanned, the biological growth plate drops into mounting platform 19, where a horizontal conveyor, such as a moving belt, ejects the plate via slot 14. A display screen 16 on scanner unit 18 of scanner 10 may display results of analysis of a plate being scanned.

Figure 2:
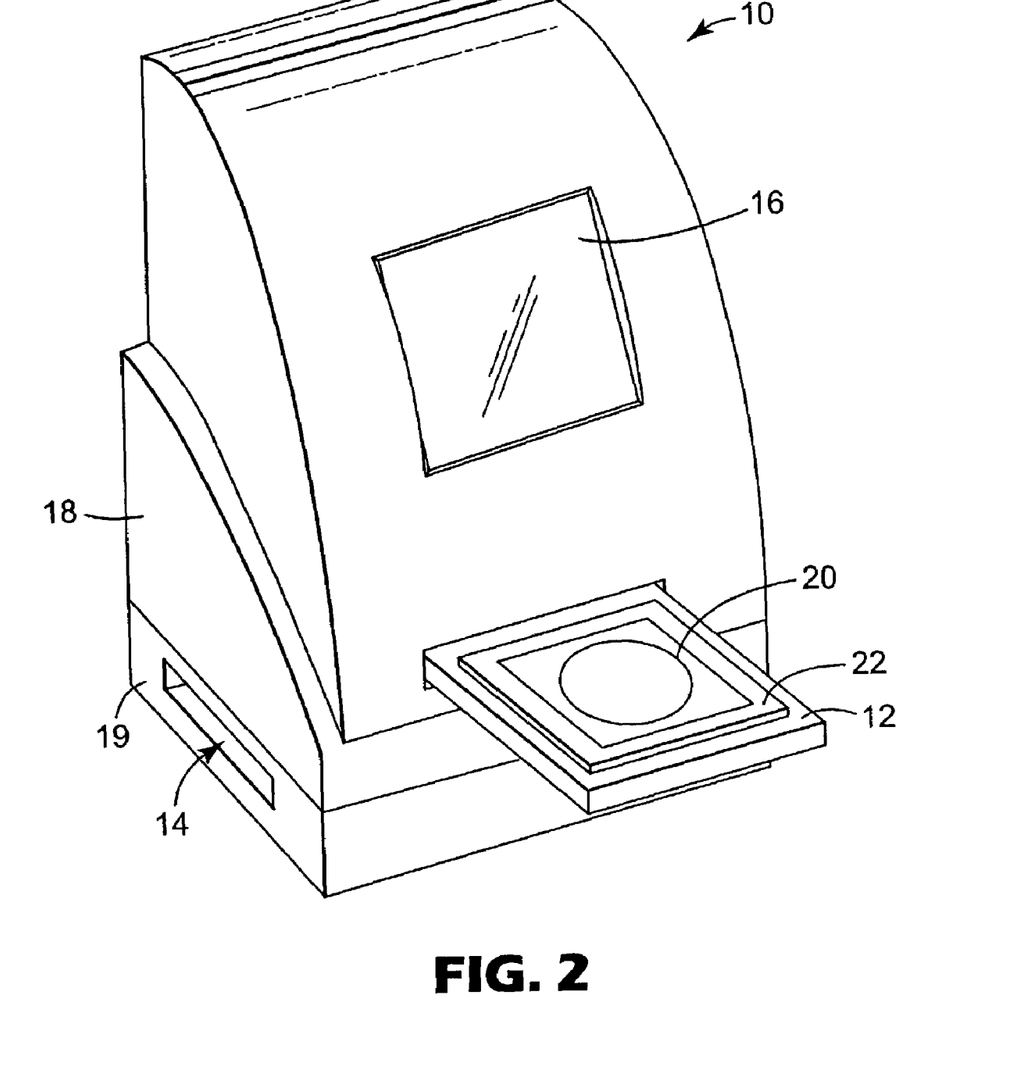
FIG. 2 is another perspective view of an exemplary biological scanner.

FIG. 2 is another perspective view of biological scanner 10. As shown in FIG. 2, drawer 12 extends outward from biological scanner 10 to receive a biological growth plate 20. As illustrated, drawer 12 may include a platform 22 on which plate 20 rests, and a set of cam levers 24, which facilitate the precise positioning of plate 20 within scanner 10. Upon placement of biological growth plate 20 on platform 22, drawer 12 retracts into scanner unit 18 to place the biological growth plate in a scanning position, i.e., a position at which the biological growth plate is optically scanned.

Figure 3:
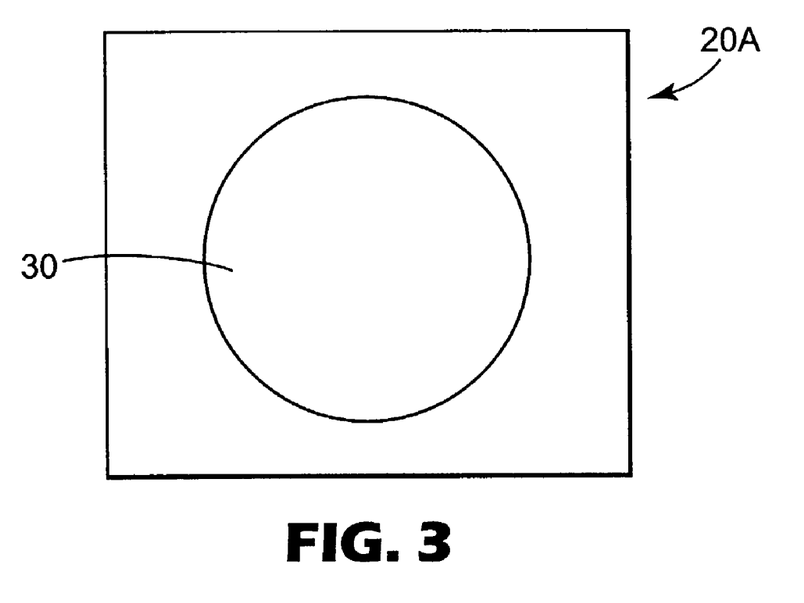
FIGS. 3 and 4 are top views of an exemplary growth plate.
Figure 4:
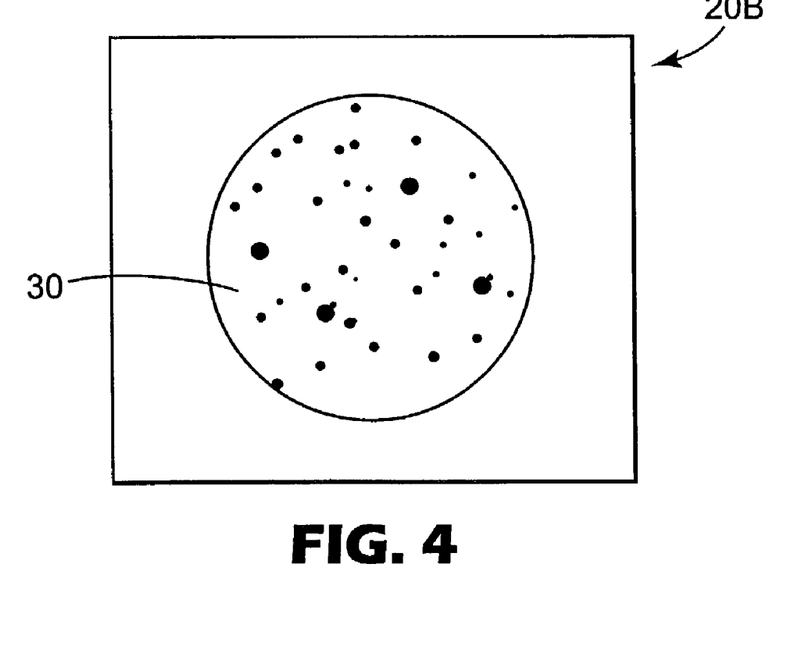

FIGS. 3 and 4 are top views of an exemplary growth plate 20. By way of example, a suitable growth plate 20 may comprise biological growth plates sold by 3M under the trade name PETRIFILM plates. Alternatively, biological growth plate 20 may comprise other biological growth plates for growing particular bacteria or other biological agents. Biological growth plates 20, for example, may facilitate the rapid growth and detection of bacteria or other biological agents including, for example, aerobic bacteria, *E. coli*, coliform, enterobacteriaceae, yeast, mold, *Staphylococcus aureus, Listeria, Campylobacter* and the like. The use of PETRIFILM plates, or other growth plates, can simplify bacterial testing of food samples. Moreover, as outlined herein, biological scanner 10 can further simplify such testing by automating the process of scanning results on a biological growth plate 20, e.g., by counting bacterial colonies on an image of the plate.

As shown in FIG. 3, a biological growth plate 20A defines a growth area 30. Optionally, growth area 30 may be a flat surface or a recessed well. A determination of whether a given sample being tested in plate 20A is acceptable, in terms of bacterial colony counts, may depend on the number of bacterial colonies per unit area. Accordingly, scanner 10 quantifies the amount of bacterial colonies per unit area on plate 20A, and may compare the amount, or "count," to a threshold. The surface of biological growth plate 20A may contain one or more growth enhancing agents designed to facilitate the rapid growth of one or more types of bacteria or other biological agents.

After placing a sample of the material being tested (typically in liquid form) on the surface of biological growth plate 20A, plate 20A can be inserted into an incubation chamber (not shown). In the incubation chamber, bacterial colonies or other biological agents being grown by growth plate 20 manifest themselves, as shown in biological growth plate 20B of FIG. 4. The colonies (represented by the various dots on biological growth plate 20B) may appear in different colors on plate 20B, which can facilitate and improve automated detection by scanner 10.

In some cases, a biological growth plate 20 may include identification (ID) markings to identify the type of biological agent being grown and tested by the given plate, or to identify the manufacturer of the plate for quality assurance purposes. Moreover, the detection and interpretation of the ID markings may be automated within biological scanner 10. For example, a processor within biological scanner 10 may implement different image processing routines or counting algorithms to count different types of bacterial colonies grown on different types of growth plates, as identified by the ID markings.

Figure 5:
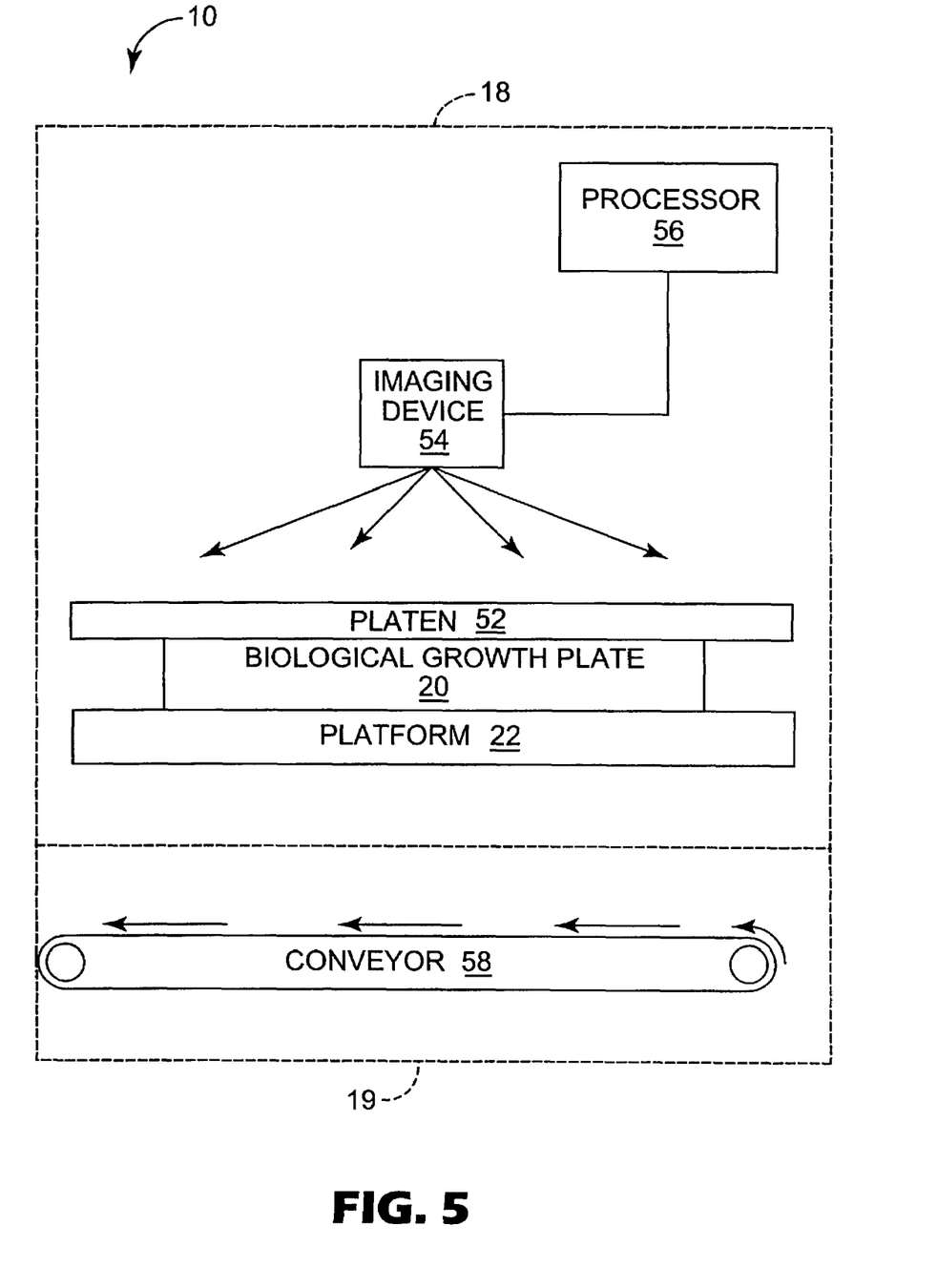
FIG. 5 is a conceptual block diagram illustrating exemplary internal components of a biological scanner.

FIG. 5 is a conceptual block diagram illustrating internal operation of biological scanner 10. As illustrated in FIG. 5, a biological growth plate 20 is positioned within biological scanner 10 on platform 22 of drawer 12 (not shown in FIG. 5). More specifically, inside scanner unit 18 of biological scanner 10, platform 22 elevates biological growth plate 20 to position the growth plate adjacent to platen 52. In other words, inside scanner unit 18 of biological scanner 10, biological growth plate 20 is sandwiched between platform 22 and platen 52. Platen 52 may define a focal plane for radiation emitted by an imaging device 54 to scan biological growth plate 20. Accordingly, platen 52 is optically transparent, permitting transmission of the radiation to the surface of growth plate 20. In some cases, platform 22 may comprise a first platen and platen 52 may comprise a second platen within biological scanner 10. In that case, it would be desirable to position the plate between the two platens, e.g., in a sandwich-like configuration, to facilitate illumination on both sides of the plate during imaging.

Imaging device 54 generates an image of biological growth plate 20 by scanning radiation across growth plate 20 and capturing reflected or transmitted radiation to form an image. In some embodiments, imaging device 54 may be formed by a collection of discrete components, including illumination subsystem and an image capture subsystem. The illumination subsystem may take the form of a variety of radiation sources such as lamps, light emitting diodes, and the like. The image capture subsystem may take the form of a line or area camera that receives reflected or transmitted radiation.

A processor 56 controls the illumination and image capture processes, and processes captured imagery to identify or enumerate the amount of biological agents in plate 20 based on the generated image. For example, imaging device 54 may comprise a camera that generates one or more digital images of biological growth plate 20 and provides the digital images to processor 56 for analysis. Processor 56 generates results, such as a bacterial colony count, and presents the results to a user, e.g., by driving display screen 16 (FIG. 1) to display the results. In addition, processor 56 may identify ID markings on plate 20, and select an appropriate image processing routine and biological analysis algorithm based on the type of plate being used. For example, the counting of bacterial colonies or other biological agents may be performed differently for different types of plates, e.g., plates used to grow different types of bacteria.

In one exemplary embodiment, platform 22 comprises a first platen that provides back illumination to biological growth plate 20 via a three color illumination system, which may incorporate red, green and blue (RGB) illumination LEDs. In that case, the RGB LEDs may provide side illumination to platform 22 and thereby provide back illumination to a biological growth plate 20 that rests on platform 22. In addition, similar RGB illumination LEDs may be used to provide top illumination of platen 52. Front illumination can be delivered to biological growth plate 20 via platen 52. Thus, platform 22 and platen 52 may collectively form an illumination chamber used to provide front and back illumination to biological growth plate 20. Exemplary front and back illumination systems are described, for example, in copending and commonly assigned U.S. application Ser. No. 10/305,722, to Graessle et al., filed Nov. 27, 2002, titled "BIOLOGICAL GROWTH PLATE SCANNER," and bearing attorney docket no. 58139US002, and U.S. application Ser. No. 10/306,663, to Graessle et al., filed Nov. 27, 2002, titled "BACK SIDE PLATE ILLUMINATION FOR BIOLOGICAL GROWTH PLATE SCANNER," and bearing attorney docket no. 58140US002, the content of each of which is incorporated herein in its entirety.

Upon illumination, imaging device 54 captures one or more images of biological growth plate 20 and provides the image(s) to processor 56 for analysis. In one example, imaging device 54 comprises a monochromatic imaging device that captures monochromatic images of biological growth plate 20. For example, biological growth plate 20 may be illuminated by one or more red LEDs, at which time imaging device 54 generates a first image. Then, biological growth plate 20 may be illuminated by one or more green LEDs, at which time imaging device 54 generates a second image. Finally, biological growth plate 20 may be illuminated by one or more blue LEDs, at which time imaging device 54 generates a third image.

Processor 56 receives the three different monochromatic images and then performs analysis on the individual images in order to generate a bacterial colony count. The use of a monochromatic imaging device 54 to generate one or more separate monochromatic images may improve image resolution for each color, and at the same time, can reduce implementation costs associated with imaging device 54. The different images can be combined by processor 56 for viewing or analysis purposes. Alternatively, or in addition, processor 56 may analyze individual images obtained during illumination with individual colors.

In some embodiments, scanner 10 may process images of different biological growth plates 20 according to different image processing profiles. The image processing profiles may be selected based on user input or identification of the type of biological growth plate 20 presented to scanner 10. The image processing profile may specify particular image capture conditions, such as illumination intensities, exposure durations, and colors, for capturing images of particular plate types. Thus, the scanner may apply different image capture conditions, including different illumination conditions, in processing images of different biological growth plates 20.

As an illustration, some types of biological growth plates 20 may require illumination with a particular color, intensity and duration. In addition, some biological growth plates 20 may require only front or back illumination, but not both. For example, an aerobic count plate may require only front illumination as well as illumination by only a single color such as red. Alternatively, an *E. coli*/Coliform plate may require only back illumination and a combination of red and blue illumination. Similarly, particular intensity levels and durations may be appropriate. For these reasons, illumination may be controlled in response to image capture conditions specified by an image processing profile.

After plate 20 has been scanned by biological scanner 10, platform 22 moves to release plate 20 onto conveyor 58, which is housed in mounting platform 19. In particular, drawer 12 (not shown in FIG. 5) re-opens to withdraw platform 22 from the scanner unit 18 of biological scanner 10. At that point, however, plate 20 may be temporarily held in place, e.g., by a clamp, pincer, securing lever, or other apparatus as outlined in greater detail below. Consequently, the subsequent movement of platform 22 from scanner unit 18 does not move plate 20 from its location adjacent platen 52. Instead, once platform 22 has been moved, the apparatus (not shown in FIG. 5) temporally holding plate 20 adjacent platen 52 can release plate 20 to fall onto conveyor 58 of mounting platform 19. Conveyor 58 ejects the biological growth plate 20 from mounting platform 19 of biological scanner 10 via slot 14 (FIG. 1).

Figure 6A:
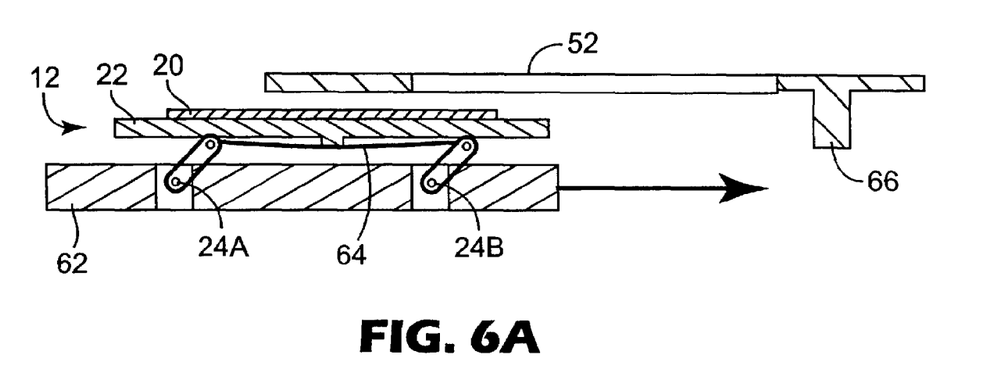
FIGS. 6A-6C are cross-sectional side views collectively illustrating operation of a loading mechanism for loading a biological growth plate into a biological scanner.
Figure 6B:
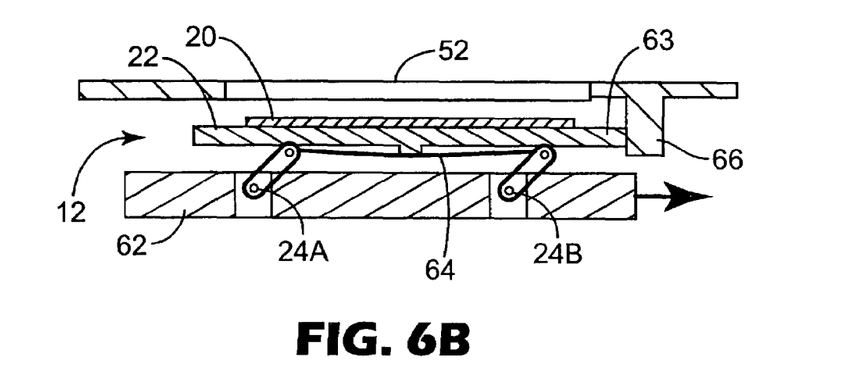
Figure 6C:
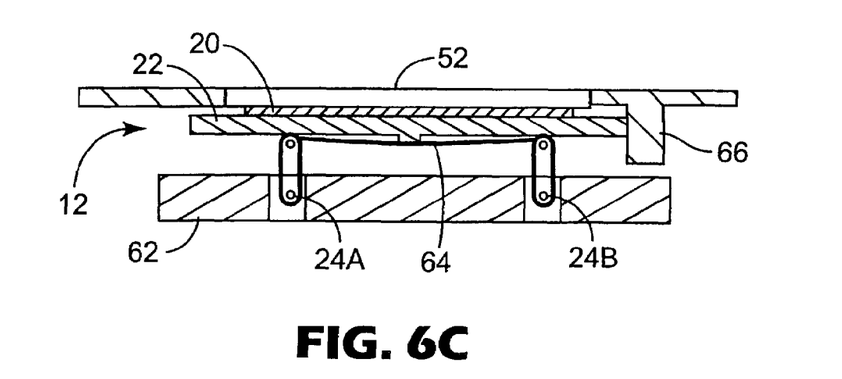

FIGS. 6A-6C are cross-sectional side views collectively illustrating the movement of a drawer 12 into the biological scanner 10, causing elevation of a biological growth plate 20 into a desired location within biological scanner 10. In particular, drawer 12 moves laterally outward from scanner unit 18 to open and thereby receive a biological plate 20 placed on platform 22 by a user. Drawer 12 then retracts into scanner unit 18 to place biological growth plate 20 in a scanning position. A motor or other suitable mechanical control mechanism can be used to actuate drawer 12 for the lateral movement which opens and closes drawer 12. To open drawer 12, a user may push inward against the drawer or depress an eject button (not shown) on scanner unit 18. Similarly, to close drawer 12, the user may again push inward against the drawer or depress the eject button. In each case, drawer 12 may be coupled to a switch that senses the force applied inward against the drawer and toward scanner unit 18 by the user. A motor or other mechanical control mechanism may be responsive to the switch to automatically open and close the door.

Drawer 12 includes a platform 22 mounted on a sliding cartridge 62 via levers 24A and 24B or another suitable attachment mechanism. Sliding cartridge 62, in turn, may attach to the motor (not shown) that causes the lateral movement of drawer 12. As an example, the motor may drive sliding cartridge 62 via a variety of mechanical transmissions, such as a lead screw or pulley arrangement. A spring 64, or the like, can be used to add a spring bias to platform 22. As illustrated in FIGS. 6A and 6B, drawer 12 moves laterally into biological scanner 10. As shown in FIG. 6B, this lateral movement (illustrated by the arrow) causes a leading edge 63 of platform 22 to abut stop 66.

Once platform 22 abuts stop 66, additional lateral movement of platform 22 is impeded, such that relative movement between sliding cartridge 62 and platform 22 causes platform 22 to elevate. More specifically, additional lateral movement of sliding cartridge 62 (from the position illustrated in FIG. 6B to that illustrated in 6C) causes levers 24 to pivot and thereby elevate platform 22 to a location adjacent platen 52. In other words, the elevation of platform 22 places plate 20 at a desired location within scanner 10, i.e., adjacent platen 52, where an image of plate 20 can be taken for analysis.

Levers 24 may be connected approximately near the four corners of platform, or a greater or fewer number of levers may be used. In any case, levers 24 can be configured to raise and lower in only one lateral direction so that once platform 22 is completely elevated, the lateral movement of sliding cartridge 62 is inhibited. Additionally, once platform 22 has elevated biological growth plate 20 to this desired location, plate spring 64 may flex to further bias plate 20 against platen 52. At this point, one or more images of biological growth plate 20 can be scanned and processed, and then used for analysis to determine the amount of biological agents grown on plate 20.

Figure 7A:
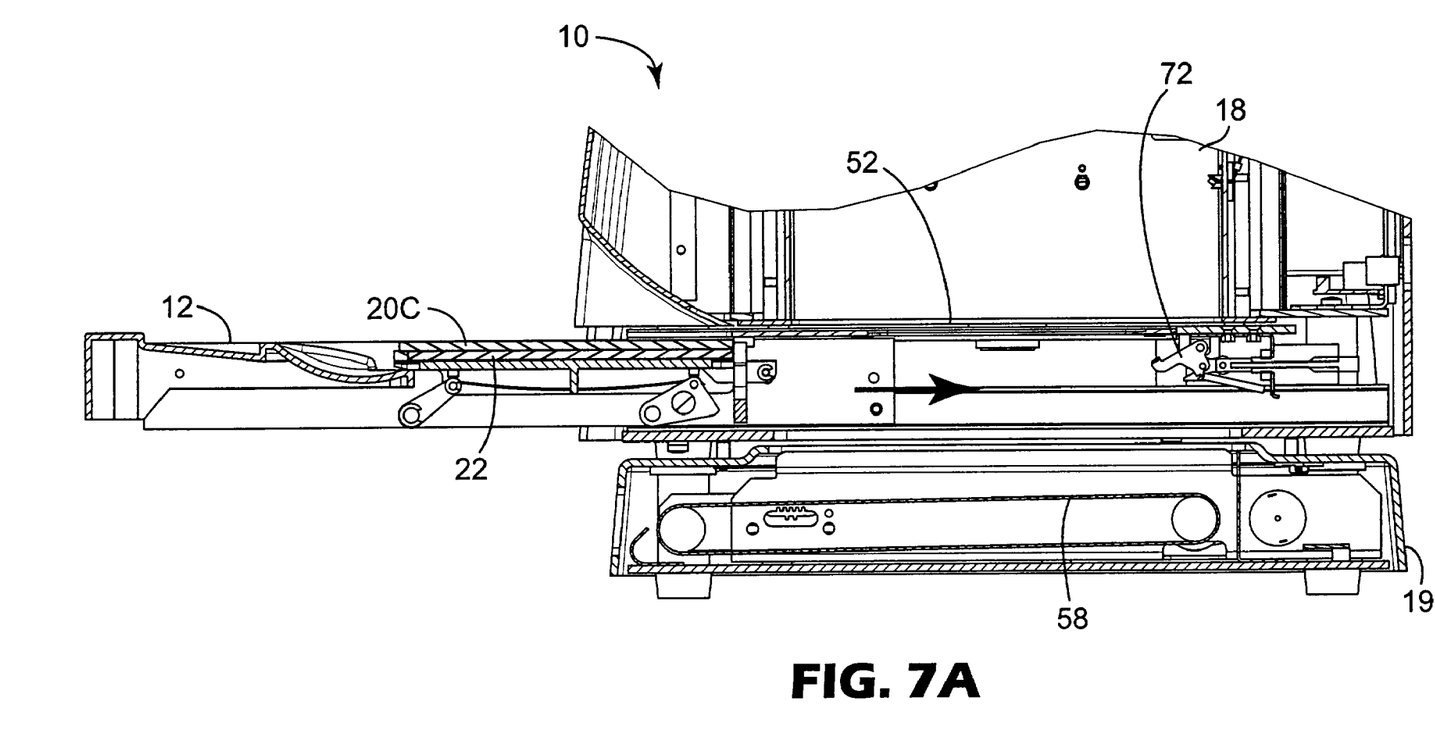
FIGS. 7A-7C are additional cross-sectional side views illustrating the operation of a loading mechanism and an ejection mechanism.
Figure 7B:
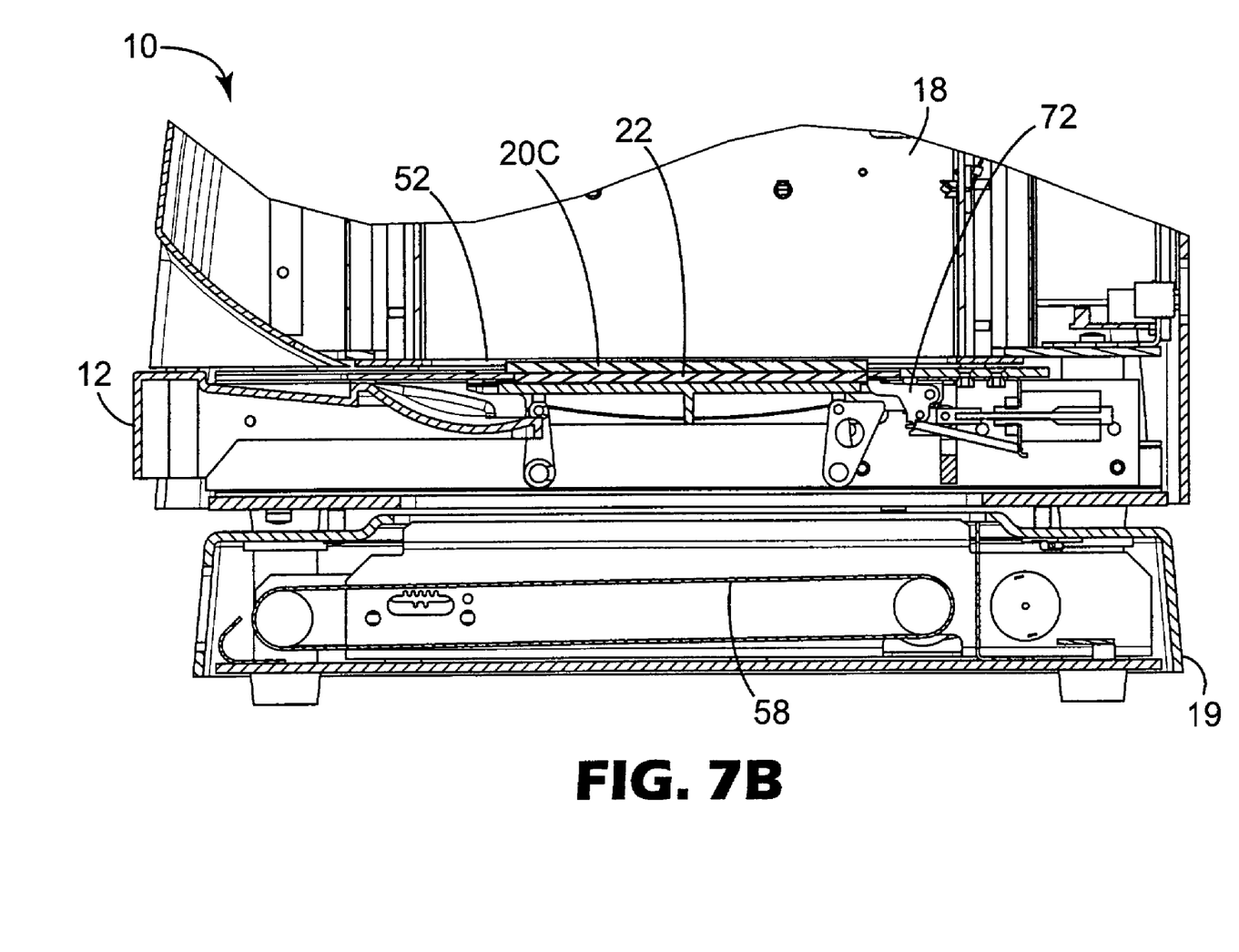
Figure 7C:
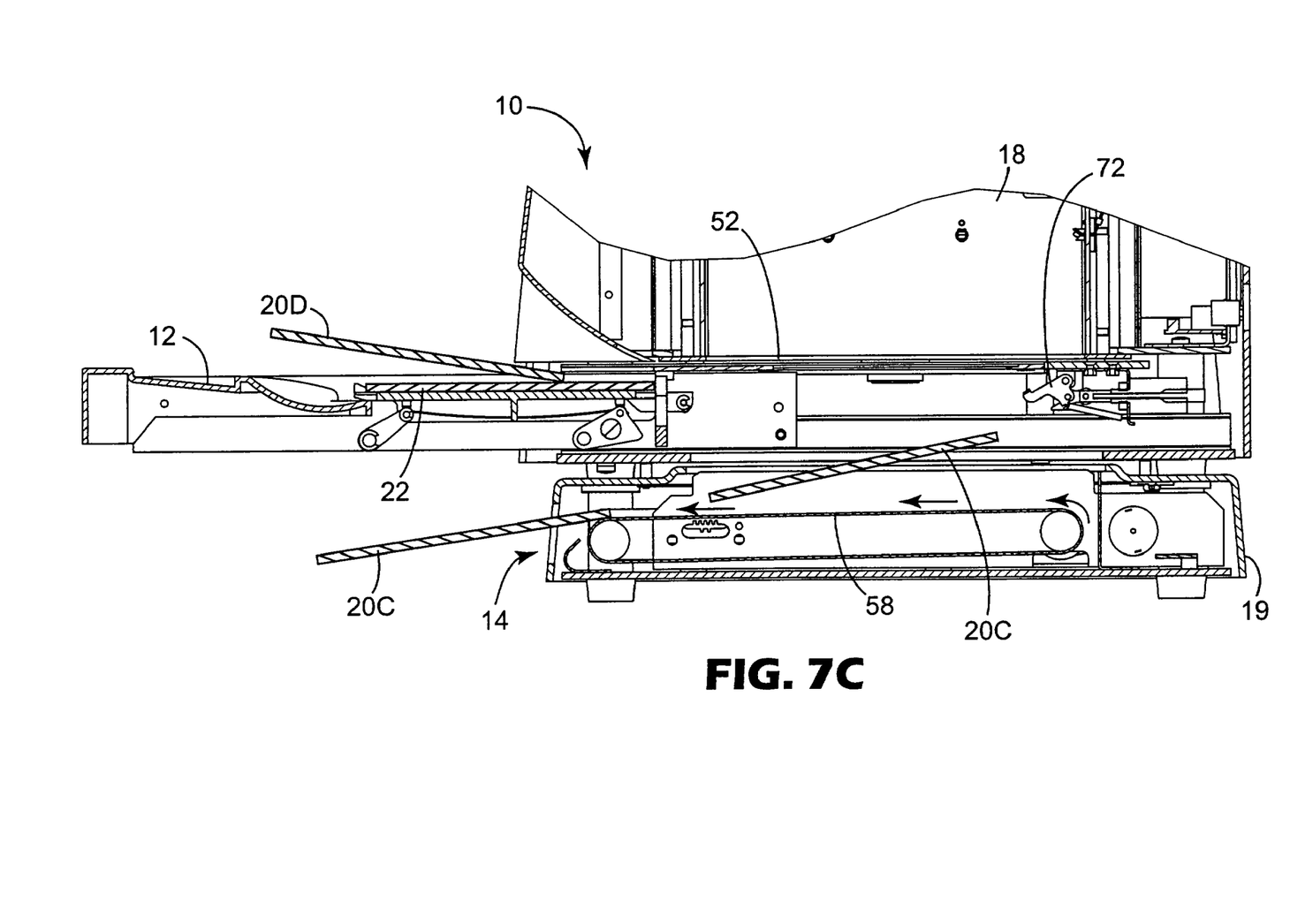

FIGS. 7A-7C are additional exemplary cross-sectional side views illustrating the movement of a drawer 12 into the biological scanner 10 and the subsequent ejection of drawer 12 from biological scanner 10. As illustrated in FIGS. 7A-7C, biological scanner 10 includes an apparatus 72 that temporarily holds a plate 20C at the location adjacent platen 52. As shown in FIG. 7A, drawer 12 moves laterally into the scanner to move plate 20C to a location where it can be imaged. FIG. 7B shows biological scanner 10 with the drawer 12 moved into the scanner unit 18 to position plate 20C. In that case, platform 22 has elevated plate 20C to the desired location where imaging can occur, i.e., adjacent platen 52.

In the example of FIGS. 7A-7C, apparatus 72 comprises a clamp, pincer, securing lever, or the like, to temporally hold plate 20C at the location adjacent platen 52. Accordingly, when drawer 12 is subsequently opened (as illustrated in FIG. 7C), apparatus 72 temporarily holds plate 20C at that same location, preventing the plate from being withdrawn from scanner unit 18 with drawer 12. In other words, when drawer 12 is subsequently opened, plate 20C does not remain on platform 22. Instead, apparatus 72 temporarily holds plate 20C at the location adjacent platen 52 when the drawer is subsequently opened. Then, once drawer 12 has opened a sufficient amount, vacating an area beneath growth plate 20C, apparatus 72 releases plate 20C, which falls onto a motor driven conveyor 58 housed within mounting platform 19 of biological scanner 10.

Conveyor 58 moves biological growth plate 20C to eject it from biological scanner 10 via ejection slot 14 in mounting platform 19. Upon projection of drawer 12 outward from scanner unit 18 and ejection of biological growth plate 20C from ejection slot 14, another biological growth plate 20D can be inserted onto platform 22 of drawer 12 for movement into biological scanner 10. In this manner, another biological growth plate 20 can be inserted into biological scanner 10, properly positioned within the scanner unit 18, imaged or otherwise scanned to identify or enumerate amounts of biological agents, and then ejected from biological scanner 10. The configuration of scanner 10 described herein, automates the insertion, positioning, and ejection of biological growth plates in a manner that ensures that reliable imaging can occur and promotes user convenience, thereby improving the integrity of automated scanning of such biological growth plates.

Figure 8A:
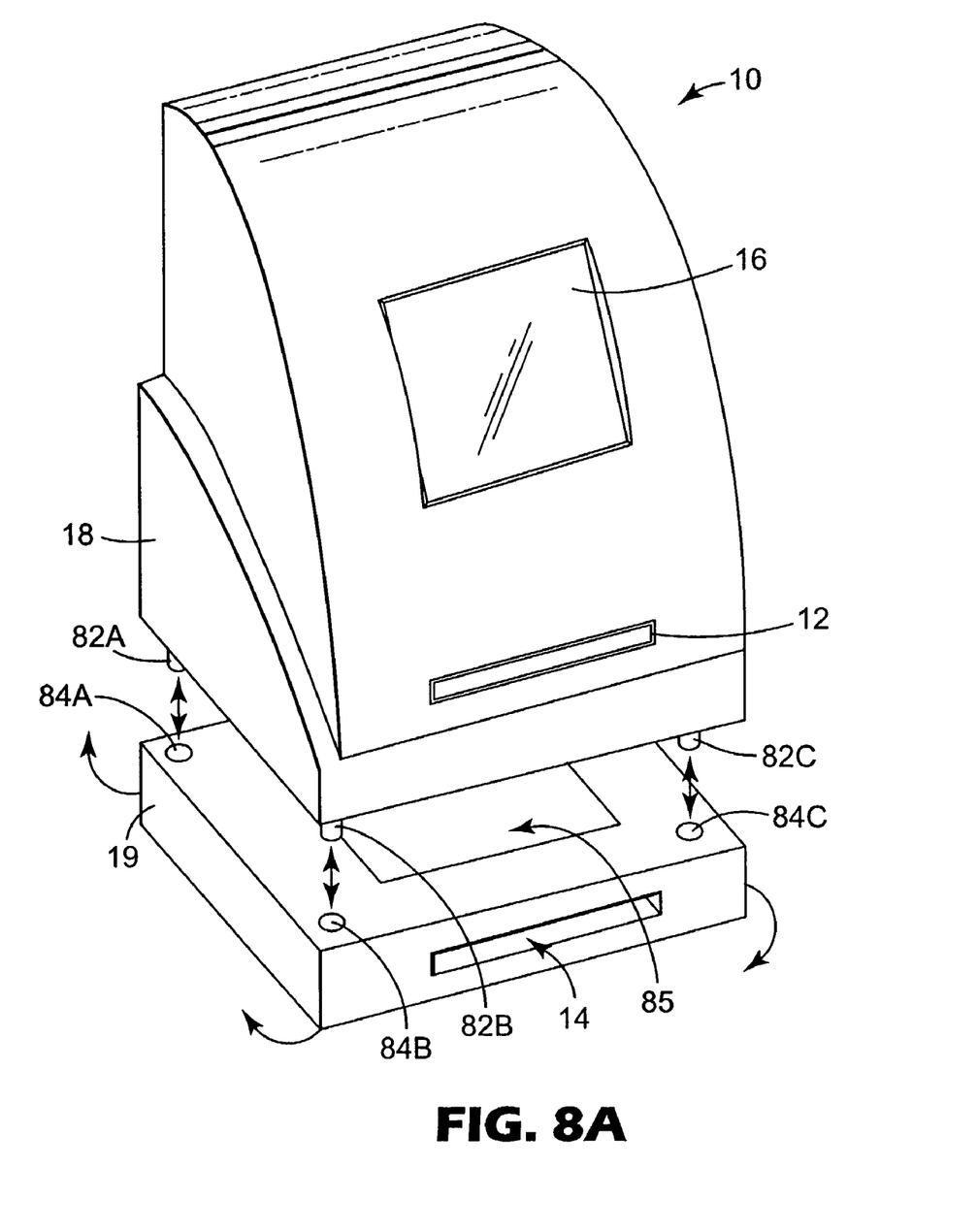
FIGS. 8A and 8B are additional perspective views of a biological scanner in accordance with another embodiment of the invention.
Figure 8B:
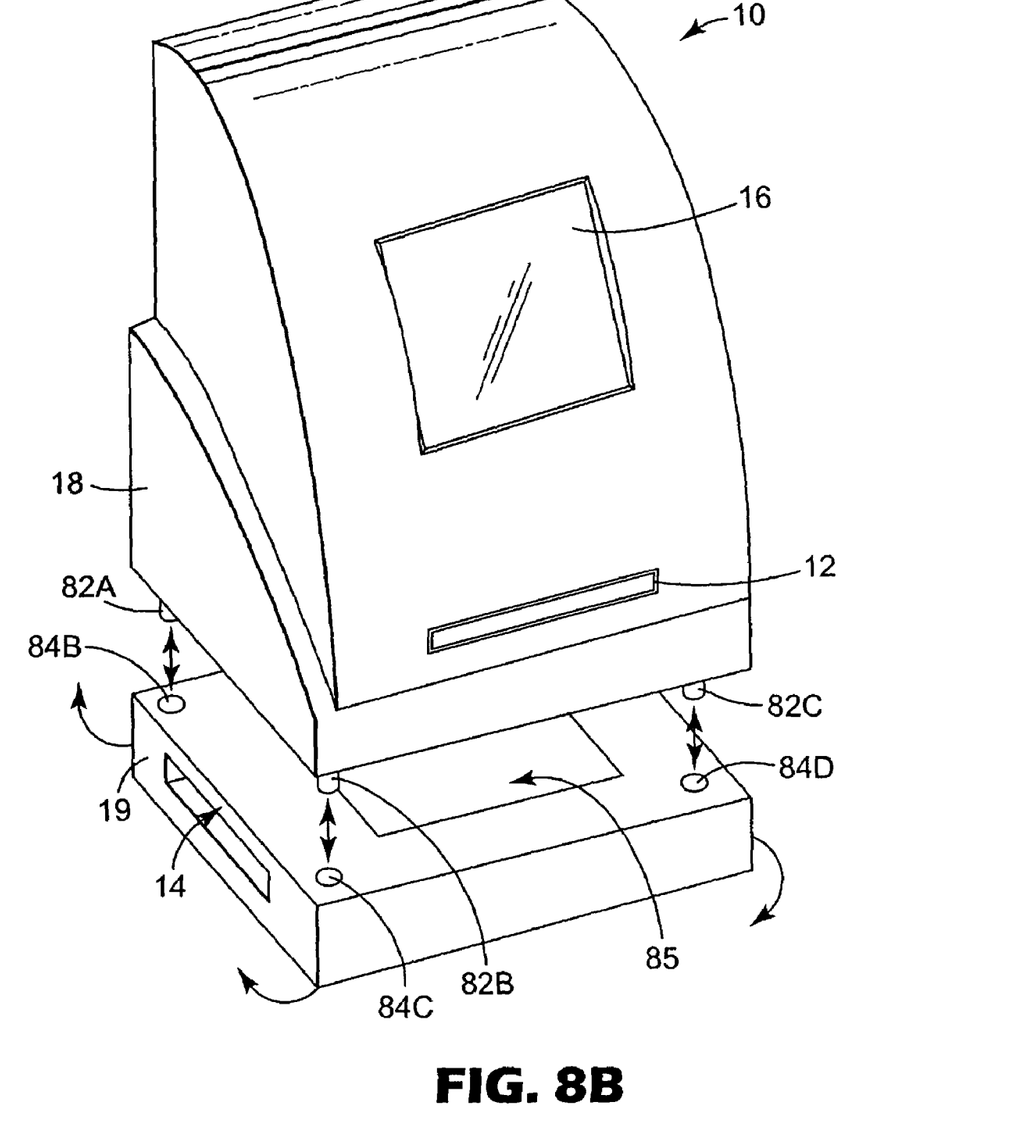

FIGS. 8A and 8B are additional perspective views of a biological scanner 10 in accordance with another embodiment of the invention. Again, biological scanner 10 includes a drawer 12 that can receive a biological growth plate, and move the plate into biological scanner 10. Biological scanner 10 also includes ejection slot 14 through which the plate 20 can be ejected following analysis. For example, following analysis of the biological growth plate 20 inside scanner unit 18, the plate 20 may be released, as outlined herein, to fall through hole 85 and into mounting platform 19. A conveyor (not shown in FIGS. 8A and 8B) housed in mounting platform 19 can then eject the plate 20 via ejection slot 14. Biological scanner 10 may also include other features, such as a display screen 16 to display the analysis of the biological plate to a user, as further shown in FIGS. 8A and 8B.

In the embodiment illustrated in FIGS. 8A and 8B, scanner unit 18 and mounting platform 19 of biological scanner 10 are detachable from one another. Furthermore, scanner unit 18 and mounting platform 19 of biological scanner 10 are re-configurable, in that scanner unit 18 and mounting platform 19 can be rotated relative to one another. In other words, scanner unit 18 and mounting platform 19 can be attached to one another in one of a plurality of different positions. Accordingly, drawer 12 of scanner unit 18 and the ejection slot 14 of mounting platform 19 can be positioned along a common side of biological scanner 10 (as illustrated in FIG. 8A), or alternatively, drawer 12 of scanner unit 18 and the ejection slot 14 of mounting platform 19 can be positioned such that they are not on a common side of biological scanner 10 (as illustrated in FIG. 8B). This reconfigurability can allow biological scanner 10 to be placed in different laboratory environments that have different space limitations or layout concerns.

In order to facilitate the attachment of scanner unit 18 to mounting platform 19 in different relative positions, scanner unit 18 may include pins 82 that mate with sockets 84 formed in mounting platform 19. Alternatively, mounting platform 19 may include the pins 82 and scanner unit 18 may be formed with the sockets 84. The term "socket," as used herein, may refer to a variety of hole, receptacle or other female terminal structures capable of engagement with a pin. The term "pin," as used herein, may refer to a variety of peg, pin, plug, protrusion or other male terminal structures capable of engagement with a socket. Pins and sockets 82, 84 form electrical interfaces for communication of power between mounting platform 19 and scanner unit 18. For example, scanner unit 18 may provide operating power to mounting platform 19. Alternatively, mounting platform 19 may provide operationg power to scanner unit 18 via pins and sockets 82, 84. In some embodiments, pins and sockets 82, 84 also may communicate control or status signals, e.g., to control operation of the conveyor in mounting platform 19. In addition to providing electrical connections, pins and sockets 82, 84 may provide mechanical positioning, alignment and registration, between scanner unit 18 and mounting platform 19.

Other cooperative engagement hardware may be provided in place of pins and sockets. In any case, the distance between any two sockets 84 along a common side of mounting platform 19 and the distance between any two pins 18 along a common side of scanner unit 18 is substantially the same. Accordingly, pins 82A and 82B of scanner unit 18 can mate with sockets 84A and 84B of mounting platform 19 when the scanner unit and mounting platform are coupled to one another in a first position as illustrated in FIG. 8A, or alternatively, pins 82A and 82B of scanner unit 18 can mate with sockets 84B and 84C of mounting platform 19 when the scanner unit and mounting platform are coupled to one another in a second position as illustrated in FIG. 8B. The mounting arrangement depicted in FIGS. 8A and 8B permits scanner unit 18 to be rotated three-hundred sixty degrees (ninety degrees between adjacent positions) between four different positions.

In some embodiments, scanner unit 18 and mounting platform 19 may have separate power supplies, e.g., separate batteries or separate AC power cords. Alternatively, a single power supply or power cord may be used. In the latter case, one or more pins 82 and one or more sockets 84 may include electrical connectors that electrically couple scanner unit 18 to mounting platform 19 and facilitate the transfer of electrical current between the scanner unit 18 and mounting platform 19. Moreover, in some embodiments, control signals may be transferred between scanner unit 18 and mounting platform 19, e.g., to control on/off switching of the conveyor within mounting platform 19 when a plate is to be ejected. Alternatively, the conveyor within mounting platform 19 may run substantially all the time when power is supplied, without being controlled by on/off switching.

In one example, one or more of the pins 82 may be "active" in the sense that they provide both an electrical interface to facilitate the transfer of electrical current, and a signal transfer interface to facilitate the transfer of control signals. Each of sockets 84 may be configured to couple with either the active pin or one of the passive pins that do not include electrical interfaces. In this manner, current and control signals can be transferred between scanner unit 18 and mounting platform 19 regardless of the relative positioning of the portions 18, 19. Many other types of electrical and control signal connections could also be used, including, for example, internal or external cords, wires, or the like.

Figure 9A:
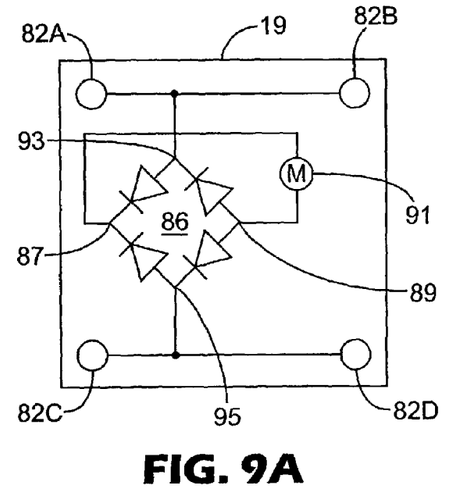
FIGS. 9A and 9B illustrate an exemplary electrical coupling configuration for a mounting platform and scanning unit of a biological scanner.
Figure 9B:
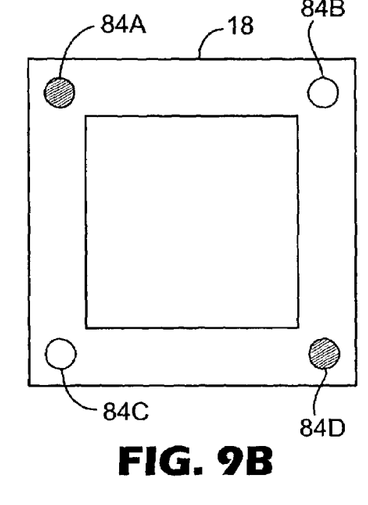

FIGS. 9A and 9B illustrate an exemplary electrical coupling configuration for a mounting platform and scanning unit of a biological scanner. In particular, FIG. 9A provides a top view of mounting platform 19 and FIG. 9B provides a bottom view of scanner unit 18. A diode rectifier bridge 86 and other electrical coupling hardware is represented functionally in FIG. 9A to depict an exemplary electrical coupling configuration. In operation, as scanner unit 18 is placed on mounting platform 19, sockets or pins 84A-84D engage reciprocal sockets or pins 82A-82D on the mounting platform. For purposes of illustration, it will be assumed that scanner unit 18 includes sockets 84 and mounting platform 19 includes pins 82.

Pins 82 engage sockets 84 upon placement of scanner unit 18 on mounting platform 19. In some embodiments, sockets 84 may define either spring-loaded electrical contacts for electrically conductive engagement with pins 82 or insulative surfaces to electrically insulate pins 82. In the example of FIG. 9B, scanner unit includes a first socket 84A having an electrical contact, a second socket 84B having an insulating surface, a third socket 84C having an insulating surface, and a fourth socket 84D having an electrical contact. Accordingly, two pins 82 from mounting platform 19 are electrically coupled to sockets 84A, 84D, depending on the orientation of scanner unit 18 relative to the mounting platform. In particular, either pin 82A or 82B is coupled to one of sockets 84A or 84D, which are mounted on diagonally opposing corners of scanner unit 10. Similarly, either pin 82C or 82D is coupled to one of sockets 84A or 84D. In this manner, one of pins 82A, 82B is electrically coupled and the other is electrically insulated, while one of pins 82C, 82D is electrically coupled and the other is electrically insulated. Insulating surfaces in sockets 84B, 84C serve to prevent shorting of the two unused pins 82 to the housing of scanner 10 or other surfaces.

Diode rectifier bridge 86 serves to deliver a steady power supply from mounting platform 19 to electronics within scanner unit 18, or vice versa, regardless of the orientation of the mounting platform and scanner unit. As shown in FIG. 9A, opposing terminals 87, 89 of diode rectifier bridge 86 are coupled across a motor 91 housed within mounting platform 19. Motor 91 drives a conveyor within mounting platform 19. Terminal 93 of diode rectifier bridge 86 is coupled to pins 82A, 82B, one of which is coupled to a conductive socket 84A, 84D in scanner unit 18. Terminal 95 of diode rectifier bridge 86 is coupled to pins 82C, 82D, one of which is coupled to a conductive socket 84A, 84D in scanner unit 18. In this manner, conductive sockets 84A, 84D receive a constant source of power from mounting platform 19 regardless of the orientation of scanner unit 18 relative to the mounting platform. Alternatively, conductive pins 82C, 82D receive a constant source of power from scanner unit 18.

Figure 10A:
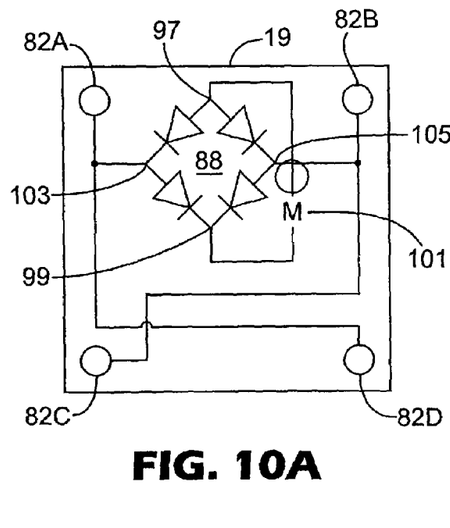
FIGS. 10A and 10B illustrate another exemplary electrical coupling configuration for a mounting platform and scanning unit of a biological scanner.
Figure 10B:
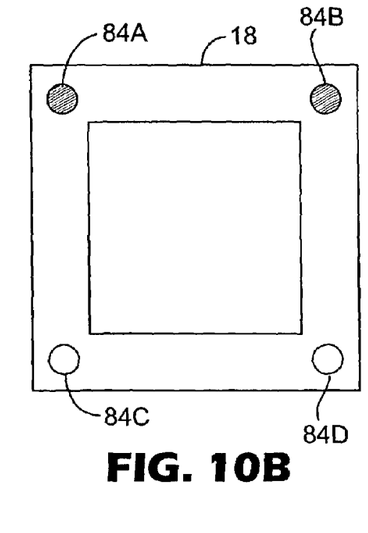

FIGS. 10A and 10B illustrate another exemplary electrical coupling configuration for mounting platform 19 and scanning unit 18 of biological scanner 10. In the example of FIGS. 10A and 10B, conductive sockets 84A, 84B in scanner unit 18 are disposed adjacent one another, i.e., on adjacent corners of the scanner unit. To support supply of power from mounting platform 19 to scanner unit 18, or vice versa, regardless of the orientation of scanner unit 18, the mounting platform includes an alternative arrangement for diode rectifier bridge 88 and pins 82.

As shown in FIG. 10A, terminals 97, 99 of diode rectifier bridge 88 are coupled across a motor 101. Also, pins 82A and 82D are electrically coupled to one another, and to terminal 103 of diode rectifier bridge 88. Similarly, pins 82B and 82C are electrically coupled to one another, and to terminal 105 of diode rectifier bridge 88. In operation, either pin 82A or 82D is coupled to one of sockets 84A or 84D, which are mounted on adjacent corners of scanner unit 10. Similarly, either pin 82B or 82C is coupled to one of sockets 84A or 84b. In this manner, one of pins 82A, 82D is electrically coupled and the other is electrically insulated, while one of pins 82B, 82C is electrically coupled and the other is electrically insulated. Again, the arrangement shown in FIGS. 10A and 10B serves to provide a continuous source of power from mounting platform 19 to scanner unit 18, or vice versa, without regard to the relative positioning of the scanner unit and the mounting platform.

In general, scanner unit 18 and mounting platform 19 of scanner 10 provide multiple possible positions. More particularly, scanner unit 18 and mounting platform 19 may permit selective relative positioning that support continued supply of power, e.g., without the need to disconnect cables or actuate switches. Instead, the user may conveniently reposition scanner unit 18 and mounting platform 19 to obtain desired plate loading and ejection orientations, which may be a function of a laboratory environment and applicable space limitations.

A number of embodiments of a biological scanner have been described. For example, techniques and structures have been described for automating the insertion of biological growth plates into a scanner and the ejection of biological growth plates from the scanner. In particular, the insertion and ejection techniques described herein can ensure that reliable imaging can occur within the biological scanner. Also, a reconfigurability feature for a biological scanner has been described in which a scanner unit of the biological scanner can be attached to a mounting platform of the scanner in one of a plurality of possible configurations. This re-configurability feature can allow the biological scanner to be placed in different laboratory environments that have different space limitations or concerns.

Nevertheless, various modifications may be made without departing from the spirit and scope of the invention. For example, one or more features described herein may be used with or without other described features. Moreover, several features described herein may be used in a biological scanner that simply generates a high quality image of the biological growth plate, and presents the high quality image to a user for analysis. In that case, a processor used to count bacterial colonies may be eliminated in favor of a less complicated processor that simply presents images to a user. In other words, the processor may simply drive a display such as display 16 (FIG. 1) to present a high quality image of the plate to a user so that the user can analyze the image and identify or enumerate the number of bacterial colonies. These and other embodiments are within the scope of the following claims.

The invention claimed is:

1. A biological scanner for scanning a biological growth plate, the scanner comprising:
    scanning means for creating an image of a biological growth plate;
    a drawer that opens to receive a biological growth medium and closes to move the medium into the scanner;
    an apparatus to temporarily hold the medium at a location inside the scanner when the drawer is subsequently opened following movement of the medium into the scanner;
    a conveyor to remove the medium from the scanner following release of the medium by the apparatus when the drawer is subsequently opened;
    a processor to coordinate functions of the scanning means, the drawer, the apparatus, and the conveyor.

2. The biological scanner of claim 1, wherein the apparatus comprises a clamp that clamps the medium after insertion of the medium and releases the medium when the drawer is subsequently opened following movement of the medium into the scanner.

3. The biological scanner of claim 1, wherein the apparatus comprises a pincer that pinches the medium after insertion of the medium and releases the medium when the drawer is subsequently opened following movement of the medium into the scanner.

4. The biological scanner of claim 1, wherein the apparatus comprises a securing lever that secures the medium after insertion of the medium and releases the medium when the drawer is subsequently opened following movement of the medium into the scanner.

5. The biological scanner of claim 1, further comprising a platen inside the scanner, wherein the medium is held adjacent the platen by the apparatus.

6. The biological scanner of claim 1, wherein the drawer includes a platform for receiving the medium.

7. The biological scanner of claim 6, further comprising a platen inside the scanner, wherein the medium is positioned adjacent the platen and the platform when the drawer is closed to move the medium into the scanner, and wherein the medium is temporarily held adjacent the platen by the apparatus when the door is subsequently opened following movement of the medium into the scanner and then released by the apparatus following the subsequent opening of the drawer.

8. The biological scanner of claim 6, wherein the platform comprises a first platen, the reader further comprising a second platen inside the scanner wherein the medium is held between the first and second platens within the scanner when the drawer is closed and temporarily held adjacent the second platen by the apparatus when the drawer is subsequently opened following movement of the medium into the scanner.

9. The biological scanner of claim 1, the scanning means further comprising:
   an illumination device inside the reader to illuminate the medium; and
   an imaging device to create an image of the medium upon illumination.

10. The biological scanner of claim 9, wherein the imaging device comprises a camera.

11. The biological scanner of claim 9, wherein the processor counts biological agents in the medium based on the image.

* * * * *